US011800976B2

(12) United States Patent
Song et al.

(10) Patent No.: US 11,800,976 B2
(45) Date of Patent: Oct. 31, 2023

(54) APPARATUS AND METHOD FOR IMAGE-BASED EYE DISEASE DIAGNOSIS

(71) Applicants: SAMSUNG SDS CO., LTD., Seoul (KR); SAMSUNG MEDICAL CENTER, Seoul (KR)

(72) Inventors: Su Jeong Song, Seoul (KR); Ji Eun Song, Seoul (KR); Joon Ho Lee, Seoul (KR); Joon Seok Lee, Seoul (KR); Soo Ah Cho, Seoul (KR)

(73) Assignees: SAMSUNG SDS CO., LTD., Seoul (KR); SAMSUNG MEDICAL CENTER, Seoul (KR)

( * ) Notice: Subject to any disclaimer, the term of this patent is extended or adjusted under 35 U.S.C. 154(b) by 252 days.

(21) Appl. No.: 17/199,609

(22) Filed: Mar. 12, 2021

(65) Prior Publication Data
US 2021/0282640 A1  Sep. 16, 2021

(30) Foreign Application Priority Data

Mar. 12, 2020 (KR) .................. 10-2020-0030613

(51) Int. Cl.
*A61B 3/12* (2006.01)
*G06T 7/00* (2017.01)

(52) U.S. Cl.
CPC .............. *A61B 3/12* (2013.01); *G06T 7/0014* (2013.01); *G06T 2207/20076* (2013.01); *G06T 2207/20081* (2013.01); *G06T 2207/20084* (2013.01); *G06T 2207/30041* (2013.01); *G06T 2207/30168* (2013.01)

(58) Field of Classification Search
CPC .................. A61B 3/12; G06T 7/0014; G06T 2207/20076; G06T 2207/20081; G06T 2207/20084; G06T 2207/30041; G06T 2207/30168
See application file for complete search history.

(56) References Cited

U.S. PATENT DOCUMENTS

2020/0202527 A1* 6/2020 Choi ...................... G06V 10/82

FOREIGN PATENT DOCUMENTS

| KR | 2020023029 A | * | 3/2020 | ............... A61B 3/10 |
| WO | WO-2019172206 A1 | * | 9/2019 | ........... A61B 3/0008 |

OTHER PUBLICATIONS

Seoul National University, Deep Learning Model for Glaucoma Diagnosis and its Stages Classification Based on Fundus Images Graduate School of Seoul National University (Year: 2019).*

(Continued)

*Primary Examiner* — Wednel Cadeau
(74) *Attorney, Agent, or Firm* — The PL Law Group, PLLC

(57) ABSTRACT

A method for an image-based eye disease diagnosis according to an embodiment includes receiving a fundus image, determining whether the fundus image is a deep diagnosis target using a deep diagnosis target classification model, and determining whether the fundus image has a disease through a preset deep diagnosis process when a result of the determination shows that the fundus image is the deep diagnosis target, or determining whether the fundus image has a disease by applying the fundus image to a general diagnosis model when the result of the determination shows that the fundus image is not the deep diagnosis target.

16 Claims, 6 Drawing Sheets

(56) References Cited

OTHER PUBLICATIONS

Cho, Deep Learning Model for Glaucoma Diagnosis and its Stages Classification Based on Fundus Images, Graduate School of Seoul National University, 2019.*

Cho, "Deep Learning Model for Glaucoma Diagnosis and its Stages Classification Based on Fundus Images", Graduate School of Seoul National University, 2019 (Year: 2019).*

* cited by examiner

402

404

APPARATUS AND METHOD FOR IMAGE-BASED EYE DISEASE DIAGNOSIS

CROSS-REFERENCE TO RELATED APPLICATION(S)

This application claims the benefit under 35 USC § 119(a) of Korean Patent Application No. 10-2020-0030613, filed on Mar. 12, 2020, in the Korean Intellectual Property Office, the entire disclosure of which is incorporated herein by reference for all purposes.

BACKGROUND

1. Field

The following description relates to a technology for diagnosing an eye disease based on a fundus image.

2. Description of Related Art

The medical field is directly related to human life, and thus requires a high degree of expertise. Even for disease diagnosis, expensive equipment or ophthalmologist is also inevitably required for the same reason. However, in recent years, there have been steady attempts to automatically diagnose diseases by using deep neural networks (deep learning) using medical images as input data. The deep neural network model trained based on the findings of ophthalmologist may not only serve as an aid for diagnosis of average ophthalmologist, but also attempt a diagnosis depending on the performance of the model. If such a model is used well, it is possible to provide an equal level of healthcare infrastructure regardless of the level of ophthalmologist and the presence or absence of expensive equipment.

In the deep neural network model for disease diagnosis, higher accuracy and sensitivity, that is, higher confidence is required than in other models due to the specialty of the medical field. In particular, a so-called false negative, which is an error where the presence of a disease fails to be indicated even though it is present, may cause a fatal consequence for the patient, and thus a means to minimize the error is required.

SUMMARY

The disclosed embodiments are intended to provide a method for an image-based eye disease diagnosis that is executed by a computing device including one or more processors and a memory storing one or more programs executed by the one or more processors, the method including: receiving a fundus image; determining whether the fundus image is a deep diagnosis target using a deep diagnosis target classification model; and determining whether the fundus image has a disease through a preset deep diagnosis process when a result of the determination shows that the fundus image is the deep diagnosis target, or determining whether the fundus image has a disease by applying the fundus image to a general diagnosis model when the result of the determination shows that the fundus image is not the deep diagnosis target.

The deep diagnosis target classification model may be trained by using a plurality of classification model training images, each labeled with a degree of diagnostic difficulty.

The degree of diagnostic difficulty may be calculated by generating N augmented images (N is a natural number of 1 or more) by randomly applying a preset image augmentation technique to each of the classification model training images, calculating the number of correct answers M (M is a natural number of 1 or more) among result values obtained by inputting the generated N augmented images to the general diagnosis model, and comparing a probability of correct answer (M/N) calculated from the number (N) of the generated augmented images and the number (M) of the correct answers with a preset reference probability.

The method may further include determining whether the fundus image is available for diagnosis using an image quality evaluation model before the determining of whether the fundus image is the deep diagnosis target.

The image quality evaluation model may be trained with a plurality of image quality evaluation model training images, each labeled with diagnostic availability.

The deep diagnosis process may include: outputting a plurality of diagnostic scores by inputting the fundus image to the deep diagnosis model; calculating a confidence interval of the diagnostic scores by using the mean and standard deviation of the diagnostic scores; and comparing the confidence interval and a reference threshold value of the deep diagnosis model.

The outputting of the plurality of diagnostic scores may include outputting the plurality of diagnostic scores by randomly applying a dropout to the deep diagnosis model or applying a test-time augmentation technique to the fundus image.

The comparing may include: determining that a disease is present in the fundus image when the comparison result indicates that a minimum value of the confidence interval is greater than the reference threshold value; determining that a disease is not present in the fundus image when the comparison result indicates that a maximum value of the confidence interval is less than the reference threshold value; and determining that additional diagnosis is required to determine presence or absence of a disease when the reference threshold value is present between the minimum value and the maximum value of the confidence interval.

In another general aspect, there is provided a method for an image-based eye disease diagnosis that is executed by a computing device including one or more processors and a memory storing one or more programs executed by the one or more processors, the method including: generating N augmented images (N is a natural number of 1 or more) by randomly applying a preset image augmentation technique to a training image; calculating the number of correct answers M (M is a natural number of 1 or more) among result values obtained by inputting the generated N augmented images to a disease diagnosis model; labeling a degree of diagnostic difficulty of the training image by calculating a probability of correct answer (M/N) from the number (N) of the generated augmented images and the number (M) of the correct answers and comparing the probability of correct answer with a preset reference probability; and training a deep diagnosis target classification model by using the training image labeled with the degree of diagnostic difficulty.

The labeling of the degree of diagnostic difficulty may include labeling the degree of diagnostic difficulty as "low" when the probability of correct answer is greater than the reference probability, and labeling the degree of diagnostic difficulty as "high" when the probability of correct answer is lower than the reference probability.

In still another general aspect, there is provided an apparatus for an image-based eye disease diagnosis, the apparatus including: one or more processors; and a memory storing one or more programs, wherein the one or more programs are executed by the one or more processors, and the one or more programs include instructions for performing operations including: receiving a fundus image; determining whether the fundus image is a deep diagnosis target using a deep diagnosis target classification model; and determining whether the fundus image has a disease through a preset deep diagnosis process when a result of the determination shows that the fundus image is the deep diagnosis target, or determining whether the fundus image has a disease by applying the fundus image to a general diagnosis model when the result of the determination shows that the fundus image is not the deep diagnosis target.

The deep diagnosis target classification model may be trained by using a plurality of classification model training images, each labeled with a degree of diagnostic difficulty.

The degree of diagnostic difficulty may be calculated by generating N augmented images (N is a natural number of 1 or more) by randomly applying a preset image augmentation technique to each of the classification model training images, calculating the number of correct answers M (M is a natural number of 1 or more) among result values obtained by inputting the generated N augmented images to the general diagnosis model, and comparing a probability of correct answer (M/N) calculated from the number (N) of the generated augmented images and the number (M) of the correct answers with a preset reference probability.

The one or more programs may include instructions for performing operations further comprising determining whether the fundus image is available for diagnosis using an image quality evaluation model, before the determining of whether the fundus image is the deep diagnosis target.

The image quality evaluation model may be trained with a plurality of image quality evaluation model training images, each labeled with diagnostic availability.

The deep diagnosis process may include: outputting a plurality of diagnostic scores by inputting the fundus image to the deep diagnosis model; calculating a confidence interval of the diagnostic scores by using the mean and standard deviation of the diagnostic scores; and comparing the confidence interval and a reference threshold value of the deep diagnosis model.

The outputting of the plurality of diagnostic scores may include outputting the plurality of diagnostic scores by randomly applying a dropout to the deep diagnosis model or applying a test-time augmentation technique to the fundus image.

The comparing may include: determining that a disease is present in the fundus image when the comparison result indicates that a minimum value of the confidence interval is greater than the reference threshold value; determining that a disease does not in the fundus image when the comparison result indicates that a maximum value of the confidence interval is less than the reference threshold value; and determining that additional diagnosis is required to determine presence or absence of a disease when the reference threshold value is present between the minimum value and the maximum value of the confidence interval.

In still another general aspect, there is provided an apparatus for an image-based eye disease diagnosis, the apparatus including: one or more processors; and a memory storing one or more programs, wherein the one or more programs are executed by the one or more processors, and the one or more programs include instructions for performing operations including: generating N augmented images (N is a natural number of 1 or more) by randomly applying a preset image augmentation technique to a training image; calculating the number of correct answers M (M is a natural number of 1 or more) among result values obtained by inputting the generated N augmented images to a disease diagnosis model; labeling a degree of diagnostic difficulty of the training image by calculating a probability of correct answer (M/N) from the number (N) of the generated augmented images and the number (M) of the correct answers and comparing the probability of correct answer with a preset reference probability; and training a deep diagnosis target classification model by using the training image labeled with the degree of diagnostic difficulty.

The labeling of the degree of diagnostic difficulty may include labeling the degree of diagnostic difficulty as "low" when the probability of correct answer is greater than the reference probability, and labeling the degree of diagnostic difficulty as "high" when the probability of correct answer is lower than the reference probability.

DETAILED DESCRIPTION

Hereinafter, specific embodiments of the present disclosure will be described with reference to the accompanying drawings. The following detailed description is provided to assist in a comprehensive understanding of the methods, devices and/or systems described herein. However, the detailed description is only for illustrative purposes and the present disclosure is not limited thereto.

In describing the embodiments of the present disclosure, when it is determined that detailed descriptions of known technology related to the present disclosure may unnecessarily obscure the gist of the present disclosure, the detailed descriptions thereof will be omitted. The terms used below are defined in consideration of functions in the present disclosure, but may be changed depending on the customary practice or the intention of a user or operator. Thus, the definitions should be determined based on the overall content of the present specification. The terms used herein are only for describing the embodiments of the present disclosure, and should not be construed as limitative. Unless expressly used otherwise, a singular form includes a plural form. In the present description, the terms "including", "comprising", "having", and the like are used to indicate certain characteristics, numbers, steps, operations, elements, and a portion or combination thereof, but should not be interpreted to preclude one or more other characteristics, numbers, steps, operations, elements, and a portion or combination thereof.

Figure 1:
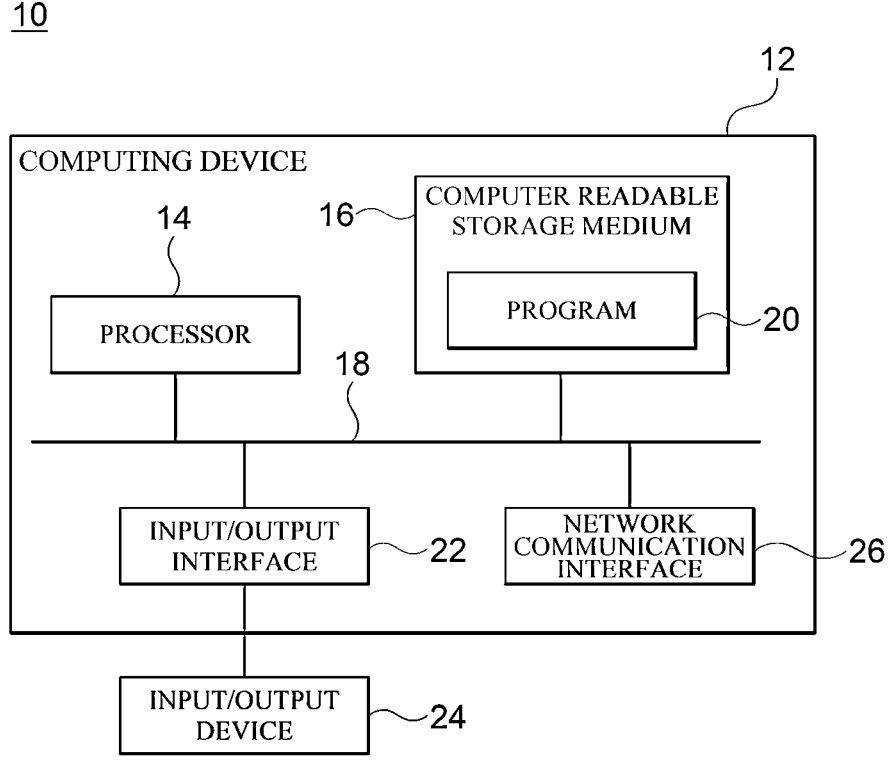
FIG. 1 is a block diagram exemplarily illustrating a computing environment that includes a computing device suitable for use in embodiments of the present disclosure.

FIG. 1 is a block diagram exemplarily illustrating a computing environment 10 that includes a computing device 5 suitable for use in embodiments of the present disclosure. In the illustrated embodiments, each component may have different functions and capabilities in addition to those described below, and additional components may be included in addition to those described below.

The illustrated computing environment 10 includes a computing device 12. In an embodiment, the computing device 12 may be the apparatus for an image-based eye disease diagnosis according to an embodiment of the present disclosure. The computing device 12 includes at least one processor 14, a computer-readable storage medium 16, and a communication bus 18. The processor 14 may cause the computing device 12 to operate according to the above-described exemplary embodiments. For example, the processor 14 may execute one or more programs stored in the computer-readable storage medium 16. The one or more programs may include one or more computer-executable instructions, which may be configured to cause the computing device 12 to perform operations (steps) according to the exemplary embodiments to be described later when executed by the processor 14.

The computer-readable storage medium 16 is configured to store computer-executable instructions or program codes, program data, and/or other suitable forms of information. A program 20 stored in the computer-readable storage medium 16 includes a set of instructions executable by the processor 14. In an embodiment, the computer-readable storage medium 16 may be a memory (a volatile memory such as a random access memory, a non-volatile memory, or any suitable combination thereof), one or more magnetic disk storage devices, optical disk storage devices, flash memory devices, other types of storage media that are accessible by the computing device 12 and may store desired information, or any suitable combination thereof.

The communication bus 18 interconnects various other components of the computing device 12, including the processor 14 and the computer-readable storage medium 16.

The computing device 12 may also include one or more input/output interfaces 22 that provide an interface for one or more input/output devices 24, and one or more network communication interfaces 26. The input/output interface 22 and the network communication interface 26 are connected to the communication bus 18. The input/output device 24 may be connected to other components of the computing device 12 via the input/output interface 22. The exemplary input/output device 24 may include a pointing device (a mouse, a trackpad, or the like), a keyboard, a touch input device (a touch pad, a touch screen, or the like), a voice or sound input device, input devices such as various types of sensor devices and/or imaging devices, and/or output devices such as a display device, a printer, a speaker, and/or a network card. The exemplary input/output device 24 may be included inside the computing device 12 as a component constituting the computing device 12, or may be connected to a computing device 102 as a separate device distinct from the computing device 12.

Figure 2:
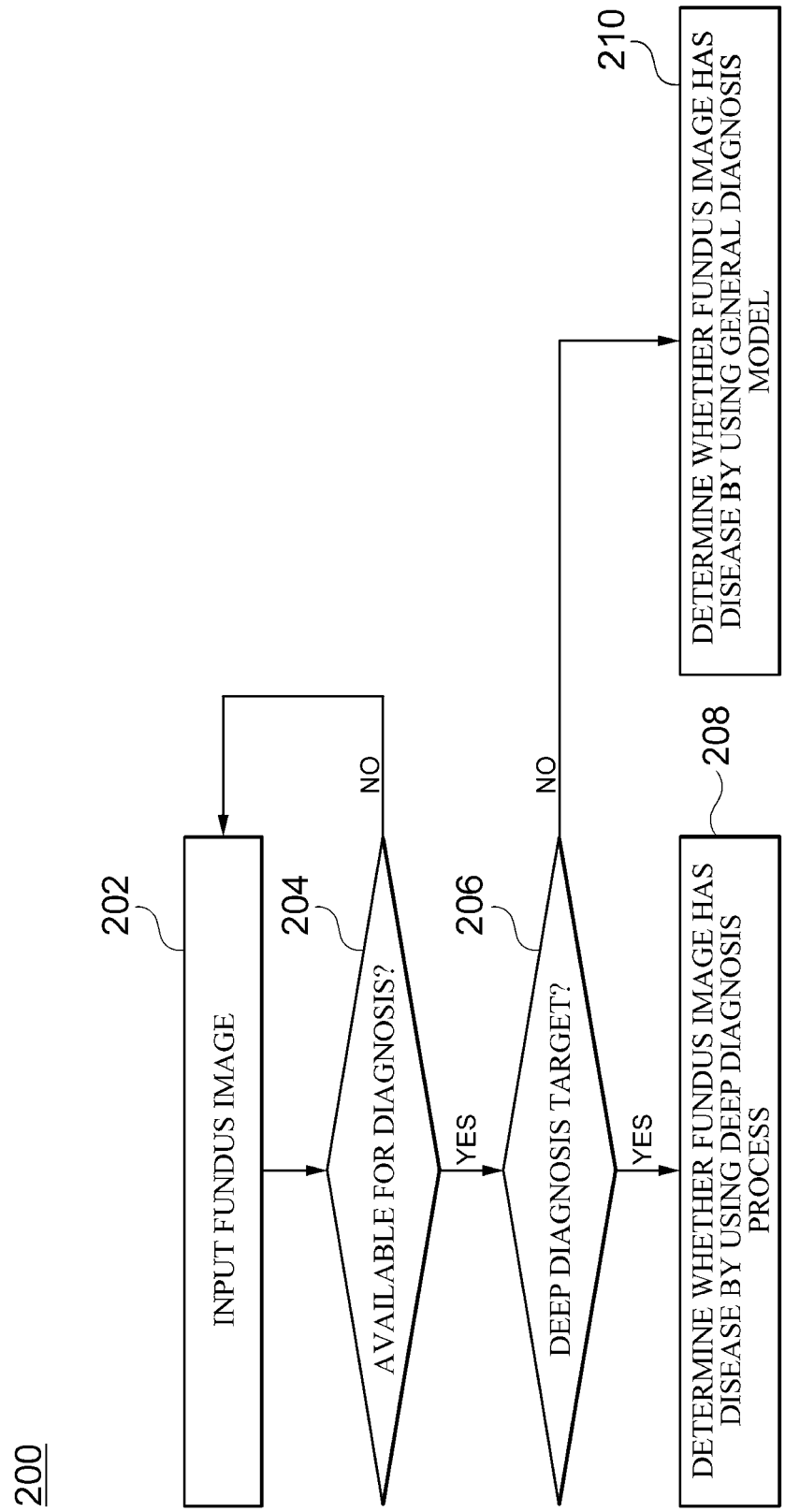
FIG. 2 is a flowchart illustrating a method for an image-based eye disease diagnosis according to an embodiment of the present disclosure.

FIG. 2 is a flowchart illustrating a method 200 for an image-based eye disease diagnosis according to an embodiment of the present disclosure. The method 200 illustrated in FIG. 2 may be performed by the computing device 12 including, for example, one or more processors, and a memory storing one or more programs executed by the one or more processors. In the illustrated flowchart, the method is divided into a plurality of steps; however, at least some of the steps may be performed in a different order, performed together in combination with other steps, omitted, performed in subdivided steps, or performed by adding one or more steps not illustrated.

In operation 202, the computing device 12 receives a fundus image.

In operation 204, the computing device 12 determines whether the input fundus image is available for disease diagnosis by using the image quality evaluation model.

In the embodiments disclosed in the present disclosure, the image quality evaluation model is a kind of a quality assessment (QA) model, and refers to a machine learning model trained with a plurality of image quality evaluation model training images, each labeled with diagnostic availability. For example, among the training images, an image may be labeled as "undiagnosable" when image characteristics such as sharpness, light blur, and image brightness are not suitable for disease diagnosis, when the image is not a fundus image, or when the main features necessary for disease diagnosis (optic disc, macular, or the like) are not displayed, and on the contrary, an image may be labeled as "diagnosable" when image characteristics are suitable for disease diagnosis, when the image corresponds to a fundus image, or when the main features necessary for disease diagnosis are well displayed. The computing device 12 may perform training on the image quality evaluation model by using the plurality of labeled image quality evaluation model training images, and may determine whether the input fundus image is available for disease diagnosis by using a trained model.

If a result of the determination in operation 204 shows that the input fundus image is an image that is not available for diagnosis, the computing device 12 returns to operation 202 and receives the fundus image again. In this case, the computing device 12 may output a message indicating that the fundus image should be captured again.

If the result of the determination in operation 204 shows that the input fundus image is an image that is available for diagnosis, in operation 206, the computing device 12 determines whether the fundus image is a deep diagnosis target by using the deep diagnosis target classification model. In this case, the deep diagnosis target classification model may be a machine learning model that is trained by using a plurality of classification model training images, each labeled with a degree of diagnostic difficulty. The deep diagnosis target classification model will be described in detail with reference to FIGS. 3 and 4.

If a result of the determination in operation 206 shows that the input fundus image is the deep diagnosis target, in operation 208, the computing device 12 diagnoses whether the fundus image has a disease through a preset deep diagnosis process.

In contrast, if the result of the determination in operation 206 shows that the input fundus image is not the deep diagnosis target, in operation 210, the computing device 12 determines whether the fundus image has a disease by applying the fundus image to a general diagnosis model. In this case, the general diagnosis model refers to a machine learning model that is trained by using a plurality of fundus images, each labeled with whether or not a disease is present, as training images.

Figure 3:
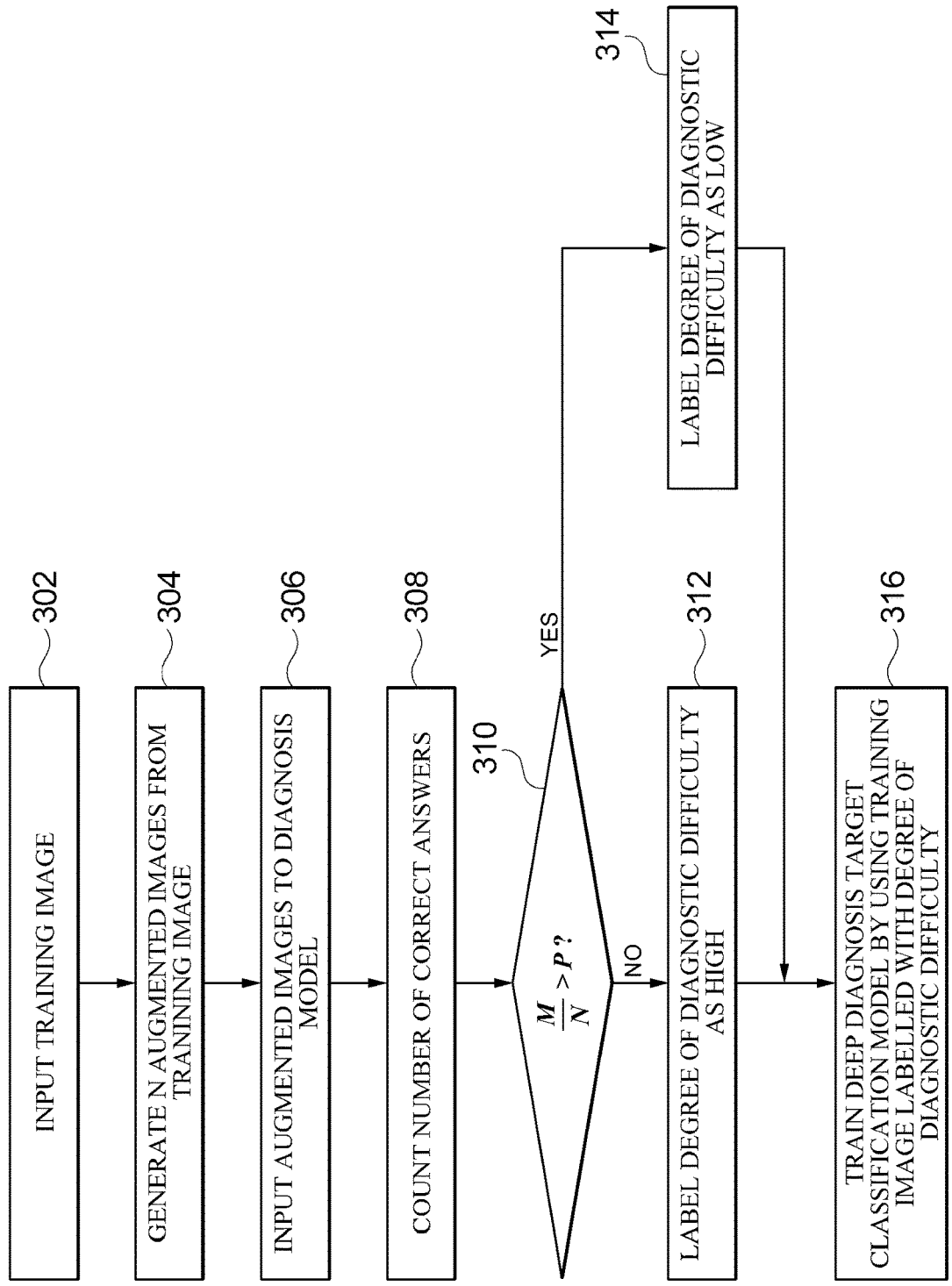
FIG. 3 is a flowchart illustrating a method of training a deep diagnosis target classification model according to an embodiment of the present disclosure.

FIG. 3 is a flowchart illustrating a method 300 of training a deep diagnosis target classification model according to an embodiment of the present disclosure. In the embodiments disclosed in the present disclosure, determination as to whether a fundus image is a deep diagnosis target is made according to the degree of diagnostic difficulty for a disease of the image, not whether the image has the disease. That is, regardless of whether or not a disease is present, the deep diagnosis target classification model according to the present disclosure classifies images with high difficulty in determining whether or not a disease is present as requiring deep diagnosis, and classifies images with low difficulty in determining whether or not a disease is present as unnecessary for deep diagnosis.

In one embodiment, the method 300 illustrated in FIG. 3 may be performed on the computing device 12 described above. That is, the computing device 12 may directly perform the method 300 of training the deep diagnosis target classification model to be described later to construct a deep diagnosis target classification model, and may use the constructed model to determine whether the input image is a deep diagnosis target. In another embodiment, the method 300 illustrated in FIG. 3 may be performed by another computing device 120. That is, in this case, the computing device 12 may receive, from another computing device, a deep diagnosis target classification model of which training has been completed, and may use the received model to determine whether the input image is a deep diagnosis target. Hereinafter, for convenience of description, it is assumed that the computing device 12 performs the method 300 of training the deep diagnosis target classification model. In the illustrated flowchart, the method is divided into a plurality of steps; however, at least some of the steps may be performed in a different order, performed together in combination with other steps, omitted, performed in subdivided steps, or performed by adding one or more steps not illustrated.

In operation 302, the computing device 12 receives a training image of the deep diagnosis classification model. At this time, the training image is an image labeled with whether or not a disease is present.

In operation 304, the computing device 12 generates N augmented images (N is a natural number of 1 or more) by randomly applying a preset image augmentation technique to the input training image.

Figure 4:
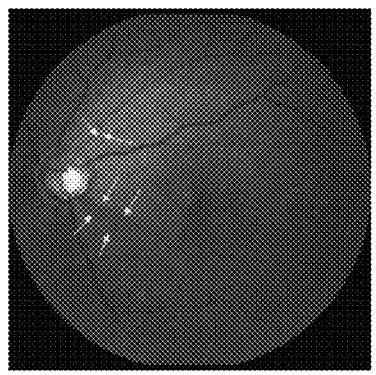
FIG. 4 is an exemplary diagram illustrating a process of augmenting a training image in a training process for a deep diagnosis target classification model according to an embodiment of the present disclosure.
Figure 4:
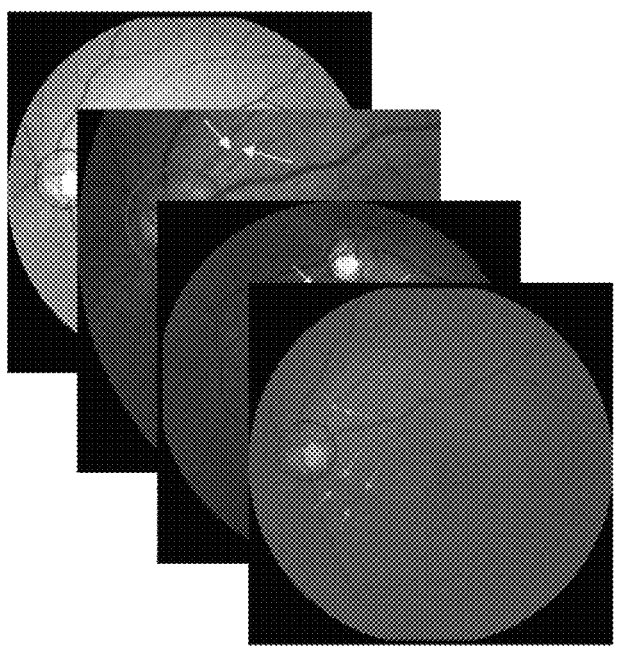

FIG. 4 is an exemplary diagram illustrating a process of augmenting a training image in a training process for a deep diagnosis target classification model according to an embodiment of the present disclosure. In an embodiment, the image augmentation technique may include all kinds of conversion technique for changing the visual characteristics of the image, such as brightness conversion, contrast conversion, color conversion, rotation, symmetry movement, translation, or cropping for the training image. The computing device 12 may generate N augmented images 404 from the training image 402 by randomly applying one or more of the image augmentation techniques. At this time, each augmented image is labeled to have the same label as the input training image. That is, when the original training image is labeled as having a disease, each of the augmented images is also labeled as having the disease.

In operation 306, the computing device 12 inputs the augmented N images to the disease diagnosis model. In an embodiment, the disease diagnosis model may be the same as the general diagnosis model described above.

In step 308, the computing device 12 compares the output value of the disease diagnosis model with the correct answer (label of the image) and calculates the number M (M is a natural number of 1 or more) of derived correct answer labels.

In operation 310, the computing device 12 calculates a correct answer probability M/N from the number N of generated augmented images and the number M of correct answers, and compares the correct answer probability M/N with a preset reference probability P. In this case, the reference probability P may be appropriately set in consideration of a performance requirement criterion of a diagnostic model, an image characteristic, and the like.

If a result of the comparison in operation 310 shows that the correct answer probability M/N is less than the reference probability, in operation 312, the computing device 12 labels the degree of diagnostic difficulty of the input training image as "high".

In contrast, if, as the result of the comparison in operation 310 shows that the correct answer probability M/N is greater than the reference probability, in operation 314, the computing device 12 labels the degree of diagnostic difficulty of the input training image as "low".

In operation 316, the computing device 12 trains the deep diagnosis target classification model by using the training image labeled with the degree of diagnostic difficulty.

Figure 5:
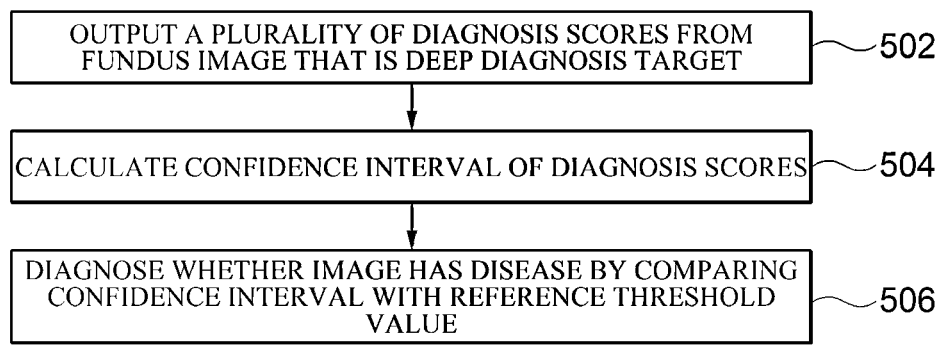
FIG. 5 is a flowchart illustrating a process of diagnosing a disease through a deep diagnosis process according to an embodiment of the present disclosure.

FIG. 5 is a flowchart illustrating a process 208 of diagnosing a disease through a deep diagnosis process according to an embodiment of the present disclosure. In the illustrated flowchart, the method is divided into a plurality of steps; however, at least some of the steps may be performed in a different order, performed together in combination with other steps, omitted, performed in subdivided steps, or performed by adding one or more steps not illustrated.

In operation 502, the computing device 12 receives a fundus image determined to require deep diagnosis and outputs a plurality of diagnostic scores from the received fundus image. Specifically, the computing device 12 may input the fundus image that is the deep diagnosis target to the disease diagnosis model to output the plurality of diagnostic scores (K numbers, K is a natural number of 2 or more). In this case, the disease diagnosis model may be the same as the above-described general diagnosis model, or may be a separate machine learning model. In addition, the diagnostic scores are output values when the fundus image is input to the disease diagnosis model, and may be a value representing a probability that a disease is present in the fundus image as a value between 0 and 1.

In an embodiment, the computing device 12 may calculate the plurality of diagnostic scores by applying a Monte-Carlo Dropout method. The Monte-Carlo dropout method is a method of deriving a plurality of diagnostic scores by randomly applying a dropout when one image is input to the disease diagnosis model. In another embodiment, the computing device 12 may calculate the plurality of diagnostic scores by using a test data augmentation technique (TTA). TTA is a method of obtaining a plurality of augmented images by randomly applying an image enhancement technique to one image, and inputting the plurality of augmented images to the disease diagnosis model to derive a plurality of diagnostic scores. In addition, the computing device 12 may obtain a plurality of diagnostic scores from the image by applying various techniques.

In operation 504, the computing device 12 calculates a confidence interval of the outputted plurality of diagnostic scores. In an embodiment, the computing device 12 may calculate a confidence interval of the diagnostic scores by using a mean m and standard deviation $\sigma$ of the diagnostic scores. For example, the confidence interval may be determined as follows.

$$m-2\sigma <= \text{confidence interval} <= m+2\sigma$$

The size of the confidence interval may be appropriately set according to the characteristics of the image and the performance requirements of the disease diagnosis model.

In step 506, the computing device 12 diagnoses whether the image has a disease by comparing the confidence interval with a reference threshold value th of the deep diagnosis model. Specifically, the computing device 12 may determine that a disease is present in the fundus image when the comparison result indicates that a minimum value of the confidence interval is greater than the reference threshold value, may determine that a disease is not present in the fundus image when the comparison result indicates that a maximum value of the confidence interval is less than the reference threshold value, and may determine that additional diagnosis is required to determine presence or absence of a disease when the reference threshold value is present between the minimum value and the maximum value of the confidence interval.

Figure 6:
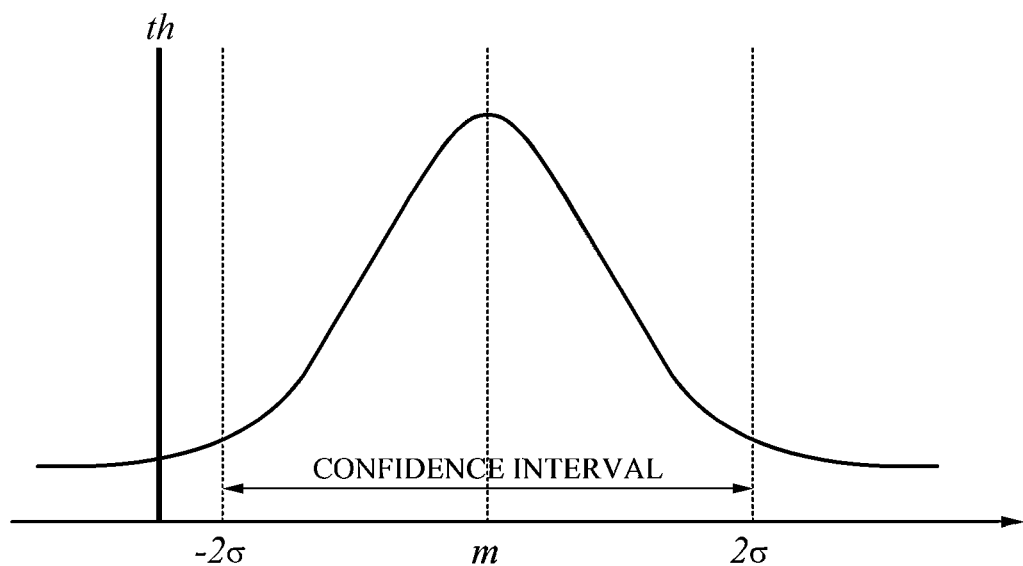
FIGS. 6 to 8 are exemplary diagrams illustrating determination as to whether a disease is present according to a relationship between a confidence interval of diagnostic scores and a reference threshold value.
Figure 7:
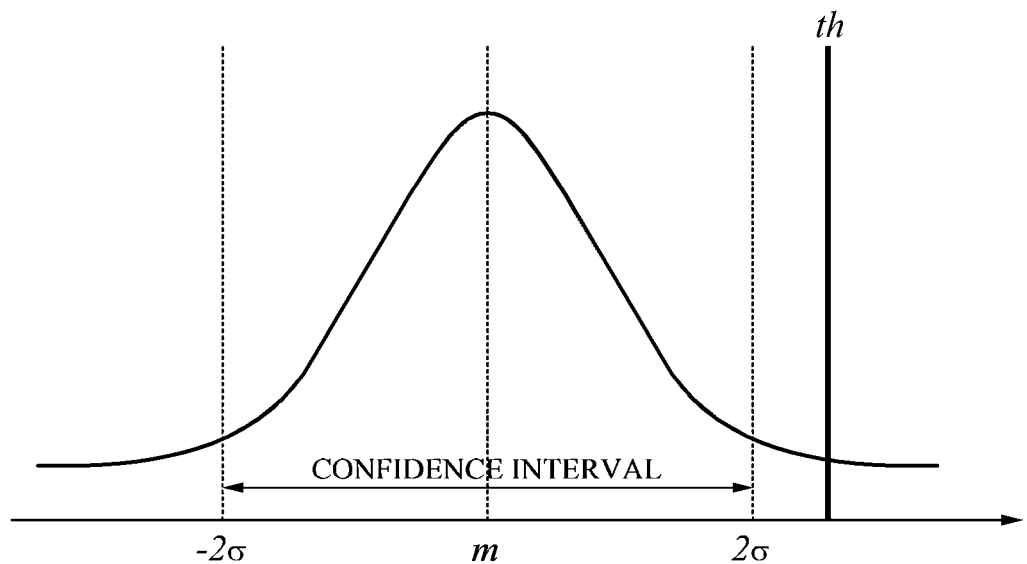
Figure 8:
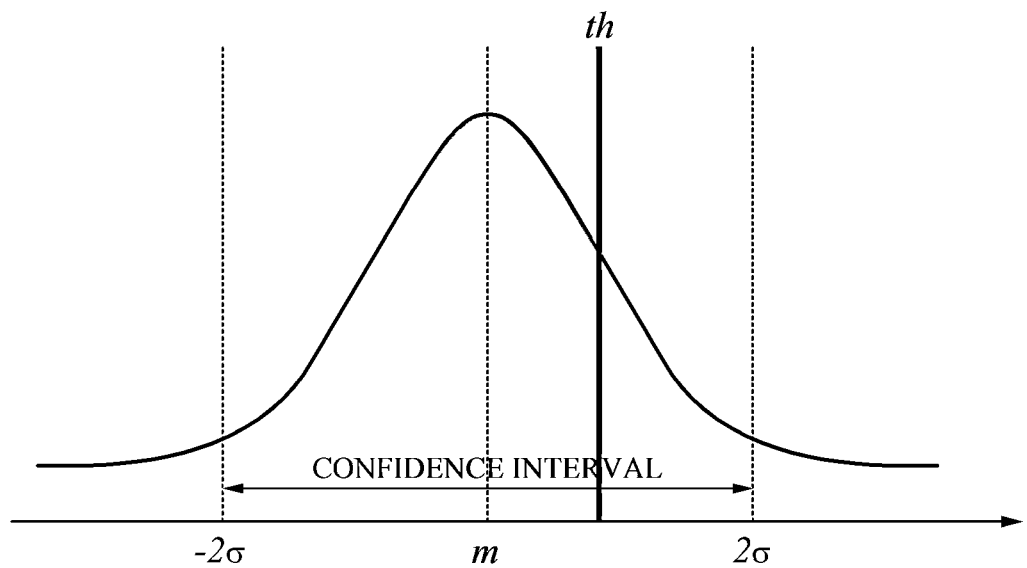

FIGS. 6 to 8 are exemplary diagrams illustrating determination as to whether a disease is present according to a relationship between a confidence interval of diagnostic scores and a reference threshold value.

First, as illustrated in FIG. 6, when the reference threshold value th for determining whether a disease is present is less than the minimum value of the confidence interval, the entire confidence interval corresponds to the disease presence interval. Therefore, in this case, the computing device 12 determines that a disease is present in the image.

First, as illustrated in FIG. 7, when the reference threshold value th for determining whether a disease is present is greater than the minimum value of the confidence interval, the entire confidence interval corresponds to the disease-free interval. Therefore, in this case, the computing device 12 determines that a disease is not present in the image.

On the other hand, as illustrated in FIG. 8, when the reference threshold value th is between the minimum and maximum values of the confidence interval, it means a case where some of the plurality of diagnostic scores indicate that a disease is present, and the others indicate that a disease is not present. That is, in this case, since there is uncertainty about whether a disease is present, the computing device 12 determines that a final diagnosis is necessary through an additional diagnosis by an ophthalmologist or the like.

According to exemplary embodiments of the present disclosure, the determination may be made as to whether the fundus image is available for the deep diagnosis by using a machine learning model trained with the disease degree of diagnostic difficulty, rather than the presence or absence of a disease in the fundus image, and the deep diagnosis process may be applied for the image with high degree of diagnostic difficulty, thereby making it possible to minimize the possibility of occurrence of both false negatives and false positives during the diagnosis process and increase the accuracy of diagnosis.

In addition, according to the embodiments disclosed in the present disclosure, the distribution of the diagnostic scores, rather than the diagnostic scores themselves, according to the machine learning model may be utilized for the final diagnosis, thereby making it possible to increase the accuracy of diagnosis and reduce diagnostic errors.

In addition, according to the embodiments disclosed in the present disclosure, images unsuitable for disease diagnosis may be automatically filtered out using the image quality evaluation model, thereby making it possible to increase the reliability of diagnosis results while automating pre-reading results of images.

Meanwhile, the embodiments of the present disclosure may include a program for performing the methods described herein on a computer, and a computer-readable recording medium including the program. The computer-readable recording medium may include program instructions, a local data file, a local data structure, or the like alone or in combination. The media may be specially designed and configured for the present disclosure, or may be commonly used in the field of computer software. Examples of computer-readable recording media include magnetic media such as hard disks, floppy disks and magnetic tapes, optical recording media such as a CD-ROM and a DVD, and hardware devices specially configured to store and execute program instructions such as a ROM, a RAM, and a flash memory. Examples of the program may include not only machine language codes such as those produced by a compiler, but also high-level language codes that can be executed by a computer using an interpreter or the like.

Although the representative embodiments of the present disclosure have been described in detail as above, those skilled in the art will understand that various modifications may be made thereto without departing from the scope of the present disclosure. Therefore, the scope of rights of the present disclosure should not be limited to the described embodiments, but should be defined not only by the claims set forth below but also by equivalents of the claims.

Meanwhile, the embodiments of the present disclosure may include a program for performing the methods described herein on a computer, and a computer-readable recording medium including the program. The computer-readable recording medium may include program instructions, a local data file, a local data structure, or the like alone or in combination. The media may be specially designed and configured for the present disclosure, or may be commonly used in the field of computer software. Examples of computer-readable recording media include magnetic media such as hard disks, floppy disks and magnetic tapes, optical recording media such as a CD-ROM and a DVD, and hardware devices specially configured to store and execute program instructions such as a ROM, a RAM, and a flash memory. Examples of the program may include not only machine language codes such as those produced by a compiler, but also high-level language codes that can be executed by a computer using an interpreter or the like.

Although the representative embodiments of the present disclosure have been described in detail as above, those skilled in the art will understand that various modifications may be made thereto without departing from the scope of the present disclosure. Therefore, the scope of rights of the present disclosure should not be limited to the described embodiments, but should be defined not only by the claims set forth below but also by equivalents of the claims.

What is claimed is:

1. A method for an image-based eye disease diagnosis that is executed by a computing device including one or more processors and a memory storing one or more programs executed by the one or more processors, the method comprising:

receiving a fundus image;

determining whether the fundus image is a deep diagnosis target using a deep diagnosis target classification model; and determining whether the fundus image has a disease through a preset deep diagnosis process when a result of the determination shows that the fundus image is the deep diagnosis target, or determining whether the fundus image has a disease by applying the fundus image to a general diagnosis model when the result of the determination shows that the fundus image is not the deep diagnosis target, wherein the determining whether the fundus image is a deep diagnosis target is made according to the degree of diagnostic difficulty for a disease of the fundus image, not whether the fundus image has the disease, wherein the deep diagnosis target classification model is trained by using a plurality of classification model training images, each labeled with a degree of diagnostic difficulty, and wherein the degree of diagnostic difficulty is calculated by generating N augmented images, where N is a natural number of 1 or more, by randomly applying a preset image augmentation technique to each of the classification model training images, calculating the number of correct answers M, where M is a natural number of 1 or more, among result values obtained by inputting the generated N augmented images to the general diagnosis model, and comparing a probability of correct answer (M/N) calculated from the number (N) of the generated augmented images and the number (M) of the correct answers with a preset reference probability.

2. The method of claim 1, further comprising determining whether the fundus image is available for diagnosis using an image quality evaluation model before the determining of whether the fundus image is the deep diagnosis target.

3. The method of claim 2, wherein the image quality evaluation model is trained with a plurality of image quality evaluation model training images, each labeled with diagnostic availability.

4. A method for an image-based eye disease diagnosis that is executed by a computing device including one or more processors and a memory storing one or more programs executed by the one or more processors, the method comprising:
 receiving a fundus image;
 determining whether the fundus image is a deep diagnosis target using a deep diagnosis target classification model; and
 determining whether the fundus image has a disease through a preset deep diagnosis process when a result of the determination shows that the fundus image is the deep diagnosis target, or determining whether the fundus image has a disease by applying the fundus image to a general diagnosis model when the result of the determination shows that the fundus image is not the deep diagnosis target,
 wherein determining whether the fundus image is a deep diagnosis target is made according to the degree of diagnostic difficulty for a disease of the fundus image, not whether the fundus image has the disease,
 wherein the deep diagnosis process includes:
 outputting a plurality of diagnostic scores by inputting the fundus image to the deep diagnosis model;
 calculating a confidence interval of the diagnostic scores by using a mean and a standard deviation of the diagnostic scores; and
 comparing the confidence interval and a reference threshold value of the deep diagnosis model.

5. The method of claim 4, wherein the outputting of the plurality of diagnostic scores includes outputting the plurality of diagnostic scores by randomly applying a dropout to the deep diagnosis model or applying a test-time augmentation technique to the fundus image.

6. The method of claim 4, wherein the comparing includes:
 determining that a disease is present in the fundus image when the comparison result indicates that a minimum value of the confidence interval is greater than the reference threshold value;
 determining that a disease is not present in the fundus image when the comparison result indicates that a maximum value of the confidence interval is less than the reference threshold value; and
 determining that additional diagnosis is required to determine presence or absence of a disease when the reference threshold value is present between the minimum value and the maximum value of the confidence interval.

7. A method for an image-based eye disease diagnosis that is executed by a computing device including one or more processors; and a memory storing one or more programs executed by the one or more processors, the method comprising:
 generating N augmented images, where N is a natural number of 1 or more, by randomly applying a preset image augmentation technique to a training image;
 calculating the number of correct answers M, where M is a natural number of 1 or more, among result values obtained by inputting the generated N augmented images to a disease diagnosis model;
 labeling a degree of diagnostic difficulty of the training image by calculating a probability of correct answer (M/N) from the number (N) of the generated augmented images and the number (M) of the correct answers and comparing the probability of correct answer with a preset reference probability; and
 training a deep diagnosis target classification model by using the training image labeled with the degree of diagnostic difficulty.

8. The method of claim 7, wherein the labeling of the degree of diagnostic difficulty includes labeling the degree of diagnostic difficulty as "low" when the probability of correct answer is greater than the reference probability, and labeling the degree of diagnostic difficulty as "high" when the probability of correct answer is lower than the reference probability.

9. An apparatus for an image-based eye disease diagnosis, the apparatus comprising:
 one or more processors; and
 a memory storing one or more programs,
 wherein the one or more programs are executed by the one or more processors; and
 the one or more programs include instructions for performing operations comprising:
 receiving a fundus image;
 determining whether the fundus image is a deep diagnosis target using a deep diagnosis target classification model; and
 determining whether the fundus image has a disease through a preset deep diagnosis process when a result of the determination shows that the fundus image is the deep diagnosis target, or determining whether the fundus image has a disease by applying the fundus image to a general diagnosis model when the result of the determination shows that the fundus image is not the deep diagnosis target,
 wherein the determining whether the fundus image is a deep diagnosis target is made according to the degree of diagnostic difficulty for a disease of the fundus image, not whether the fundus image has the disease, wherein the deep diagnosis target classification model is trained by using a plurality of classification model training images, each labeled with a degree of diagnostic difficulty, and wherein the degree of diagnostic difficulty is calculated by generating N augmented images, where N is a natural number of 1 or more, by randomly applying a preset image augmentation technique to each of the classification model training images, calculating the number of correct answers M, where M is a natural number of 1 or more, among result values obtained by inputting the generated N augmented images to the general diagnosis model, and comparing a probability of correct answer (M/N) calculated from the number (N) of the generated augmented images and the number (M) of the correct answers with a preset reference probability.

10. The apparatus of claim 9, wherein the one or more programs include instructions for performing operations further comprising determining whether the fundus image is available for diagnosis using an image quality evaluation model, before the determining of whether the fundus image is the deep diagnosis target.

11. The apparatus of claim 10, wherein the image quality evaluation model is trained with a plurality of image quality evaluation model training images, each labeled with diagnostic availability.

12. An apparatus for an image-based eye disease diagnosis, the apparatus comprising: one or more processors; and
a memory storing one or more programs,
wherein the one or more programs are executed by the one or more processors; and
the one or more programs include instructions for performing operations comprising:
receiving a fundus image;
determining whether the fundus image is a deep diagnosis target using a deep diagnosis target classification model; and
determining whether the fundus image has a disease through a preset deep diagnosis process when a result of the determination shows that the fundus image is the deep diagnosis target, or determining whether the fundus image has a disease by applying the fundus image to a general diagnosis model when the result of the determination shows that the fundus image is not the deep diagnosis target,
wherein determining whether the fundus image is a deep diagnosis target is made according to the degree of diagnostic difficulty for a disease of the fundus image, not whether the fundus image has the disease,
wherein the deep diagnosis process includes:
outputting a plurality of diagnostic scores by inputting the fundus image to the deep diagnosis model;
calculating a confidence interval of the diagnostic scores by using a mean and a standard deviation of the diagnostic scores; and
comparing the confidence interval and a reference threshold value of the deep diagnosis model.

13. The apparatus of claim 12, wherein the outputting of the plurality of diagnostic scores includes outputting the plurality of diagnostic scores by randomly applying a dropout to the deep diagnosis model or applying a test-time augmentation technique to the fundus image.

14. The apparatus of claim 12, wherein the comparing includes:
determining that a disease is present in the fundus image when the comparison result indicates that a minimum value of the confidence interval is greater than the reference threshold value;
determining that a disease is not present in the fundus image when the comparison result indicates that a maximum value of the confidence interval is less than the reference threshold value; and
determining that additional diagnosis is required to determine presence or absence of a disease when the reference threshold value is present between the minimum value and the maximum value of the confidence interval.

15. An apparatus for an image-based eye disease diagnosis, the apparatus comprising:
one or more processors; and
a memory storing one or more programs,
wherein the one or more programs are executed by the one or more processors; and
the one or more programs include instructions for performing operations comprising:
generating N augmented images, where N is a natural number of 1 or more, by randomly applying a preset image augmentation technique to a training image;
calculating the number of correct answers M, where M is a natural number of 1 or more, among result values obtained by inputting the generated N augmented images to a disease diagnosis model;
labeling degree of diagnostic difficulty of the training image by calculating a probability of correct answer (M/N) from the number (N) of the generated augmented images and the number (M) of the correct answers and comparing the probability of correct answer with a preset reference probability; and
training a deep diagnosis target classification model by using the training image labeled with the degree of diagnostic difficulty.

16. The apparatus of claim 15, wherein the labeling of the degree of diagnostic difficulty includes labeling the degree of diagnostic difficulty as "low" when the probability of correct answer is greater than the reference probability, and labeling the degree of diagnostic difficulty as "high" when the probability of correct answer is lower than the reference probability.

* * * * *